(12) United States Patent
Oishi et al.

(10) Patent No.: US 6,422,067 B1
(45) Date of Patent: Jul. 23, 2002

(54) SLURRY USEFUL FOR WIRE-SAW SLICING AND EVALUATION OF SLURRY

(75) Inventors: Hiroshi Oishi; Keiichiro Asakawa; Junichi Matsuzaki, all of Annaka; Akio Ashida, Tokyo, all of (JP)

(73) Assignees: Super Silicon Crystal Research Institute Corporation; Ohtomo Chemical Industrial Corporation, both of (JP)

( * ) Notice: Subject to any disclaimer, the term of this patent is extended or adjusted under 35 U.S.C. 154(b) by 0 days.

(21) Appl. No.: 09/637,752

(22) Filed: Aug. 11, 2000

(51) Int. Cl.[7] .................. G01N 11/14; G01N 19/02; B23D 25/02; B23D 1/04
(52) U.S. Cl. .............. 73/54.28; 73/7; 125/21; 83/307.1
(58) Field of Search .............. 73/54.28, 54.32, 73/104, 7; 125/16.01, 21; 156/353; 83/307.1, 651.1

(56) References Cited

U.S. PATENT DOCUMENTS

| | | | | |
|---|---|---|---|---|
| 4,052,278 A | * | 10/1977 | Brown et al. ............... 523/300 |
| 4,442,707 A | * | 4/1984 | Tuzson ........................... 73/86 |
| 5,799,643 A | * | 9/1998 | Miyata et al. ................. 125/21 |
| 5,937,844 A | * | 8/1999 | Kiuchi et al. ............. 125/16.02 |
| 6,001,265 A | * | 12/1999 | Toyama et al. ............... 210/712 |
| 6,006,738 A | * | 12/1999 | Itoh et al. ...................... 125/21 |
| 6,053,158 A | * | 4/2000 | Miyata et al. ................. 125/21 |
| 6,062,209 A | * | 5/2000 | Oishi ....................... 125/16.01 |
| 6,113,473 A | * | 9/2000 | Costantini et al. ............. 451/60 |
| 6,161,533 A | * | 12/2000 | Katsumata et al. ............ 125/21 |
| 6,182,729 B1 | * | 2/2001 | Banzawa et al. ............ 156/353 |
| 6,221,814 B1 | * | 4/2001 | Kaburagi et al. ........... 508/136 |

* cited by examiner

Primary Examiner—Herzon Williams
Assistant Examiner—Jay L. Politzer
(74) Attorney, Agent, or Firm—Webb Ziesenheim Logsdon Orkin & Hanson, P.C.

(57) ABSTRACT

Slurry useful for wire-saw slicing has viscosity adjusted to 400–700 mPa·second at a shear speed of 2/second and of 50–300 mPa·second at a shear speed of 380/second. The viscosity of slurry is measured using a cone and plate type viscometer which can measure viscosity at different shear speeds. Since the slurry sufficiently flows into inner parts of grooves formed in an ingot and consumed for wire-saw slicing due to the viscosity controlled in response to the shear speed, the ingot can be efficiently sliced to wafers or discs.

1 Claim, 2 Drawing Sheets

PRIOR ART

SLURRY USEFUL FOR WIRE-SAW SLICING AND EVALUATION OF SLURRY

BACKGROUND OF THE INVENTION

1. Field of the Invention

The present invention relates to slurry useful for wire-saw slicing a silicon ingot, a compound semiconductor block, a quartz block or the like, and also-relates to a method of evaluating such slurry.

2. Brief Description of the Prior Art

After top and tail parts are cut off a silicon ingot produced by a pulling method or the like, the silicon ingot is processed in the steps of outer diameter grinding, orientation flat processing, etc., and then sliced to wafers of a predetermined thickness. Although a slicer equipped with an inner blade has been used so far for slicing the ingot, a wire-sawing machine using a piano wire is used for slicing a big-size ingot.

As shown in FIG. 1, a conventional wire-sawing machine has generally three grooved rollers 1–3, one of which is coupled to a driving motor 4. A wire 5 is pulled out of a wire reel 6, wound several times around the grooved rollers 1–3, and led to another wire reel 7. A tension is applied to the wire 5 by a tensioner 8, so that the wire 5 travels in a stretched state around the grooved rollers 1–3.

An ingot 9 to be sliced is mounted to a holder 10 using a mounting jig located between the grooved rollers 1 and 2. The ingot 9 is sliced to a plurality of wafers by the wire 5. During slicing, slurry 11 is supplied to the wire 5 so as to facilitate slicing motion. The slurry 11 is fed from a slurry tank 12 through a supply pipe 13 and a nozzle 14 to the wire 5, recovered in a pan 15, and then returned to the slurry tank 12. The slurry 11 is circulated between the slurry tank 12 and a heat exchanger 16, in order to cool the slurry 11.

Such the slurry 11 is fed to inner parts of the ingot 9 in the state that grits are uniformly dispersed in a coolant, in order to slice the ingot 9 to a plurality of wafers with the wire 5. It is also an important factor that the grit-dispersing state is stable enough to avoid fluctuation of slicing conditions. In addition, the slurry 11 remaining on wafers cut off the ingot 9 shall be easily removed away from surfaces of the wafers.

Such slurry for wire-saw slicing is merely evaluated by viscosity, specific gravity and a pH value. The viscosity is commonly measured by a axial cylinder type viscometer 30 (Type-B viscometer) as shown in FIG. 2. An inner cylinder 31, which is hung from a stator 34 with a metal rod 33, is concentrically located in a vessel 32 (an outer cylinder). Sample slurry S is poured in a space between the inner cylinder 31 and the outer cylinder 32, and the outer cylinder 32 is rotated at a predetermined rotation speed. A force, which is corresponding to viscosity of the sample slurry S and along the rotating direction of the outer cylinder 32, is applied to the inner cylinder 31 by the rotating motion of the outer cylinder 32. Due to the force, a torsional moment (a torque) is applied to the metal rod 33. A scale disc 35 provided at the metal rod 33 is rotated in proportional to the torsion value. The viscosity of the sample slurry S is judged by reading a rotation angle of the scale disc.

Specific gravity is measured by a float balance-type hydrometer. A pH value is measured by an electrode-type pH meter.

Properties measured in these ways do not accurately represent an actual state of the slurry 11 which is being used for wire-saw slicing the ingot 9, so that slicing performance can not be forecast from those properties. Use of improper slurry sometimes causes various defects such as breakdown of the wire 5, damage of wafers, sticking of wafers cut off the ingot 9 and accumulation of the slurry 11 in the wire-sawing machine. In this regard, the slurry is evaluated by an actual ingot-slicing test. However, the test for researching ingot-slicing conditions needs plenty of time and cost. Such the troublesome test shall be avoided accounting the tendency that the ingot 9 is bigger and bigger in diameter.

SUMMARY OF THE INVENTION

The present invention is accomplished for elimination of the aforementioned problems and aims at a slurry suitable for wire-saw slicing without necessity of an ingot-slicing test by measuring flow characteristics (rheology) of slurry effective for ingot-slicing.

According to the present invention, slurry for slicing an ingot is evaluated by measuring viscosity of the slurry under conditions different in a shear speed using a cone and plate type viscometer. Flow characteristics (rheology) of the slurry is calculated from measured viscosity values.

The viscosity of the slurry measured by the cone and plate type viscometer is useful as a value for forecasting fluidization of the slurry during wire-saw slicing an ingot. Especially, such slurry, which has viscosity adjusted to approximately 400–700 mPa·second at a shear speed of approximately 2/second and to approximately 50–300 mPa·second at a shear speed of approximately 380/second, is suitable for wire-saw slicing an ingot.

PREFERRED EMBODIMENT OF THE INVENTION

Slurry for wire-saw slicing is classified as oily type and an aqueous type.

Oily slurry, which is prepared by suspending grits such as SiC of approximately 20 μm in diameter in a dispersion medium (an oily coolant) mainly composed of mineral oil, has been commonly used. The oily slurry has such the merit that grits are suspended in a stable state and is relatively cheap, but unfavorably inflammable. Due to flammability, the oily slurry is not proper for long-time unmanned operation. Use of the oily slurry also makes it difficult to wash and clarify wafers cut off the ingot as well as a wire-sawing machine. In addition, incineration of waste slurry at a final stage would cause harmful influences on the environment.

Aqueous slurry, which is prepared by suspending grits in an aqueous coolant, is not flammable and has such the merits that wafers and a wire-sawing machine can be easily washed and clarified by water and that waste slurry can be biologically decomposed. However, it is difficult to keep grits in a stable dispersed state.

Any type of slurry shall fulfil the requisitions as follows: An ingot can be sliced to wafers without snapping of a wire or damage of wafers. The wire can be separated from the ingot and the wafers after slicing operation is finished. The wafers cut off the ingot can be easily separated from each other. Grits are not accumulated in a wire-sawing machine. The wafers cut off the ingot have good dimensional accuracy such as medium thickness and total thickness variation (TTV). The slurry varies its viscosity within a small range during slicing.

Viscosity, specific gravity and a pH value of slurry are important properties for well performance of the slicing operation. Especially, the viscosity is a factor which puts significant influences on supply of the slurry to a contact plane between the ingot and the wire.

Figure 1:
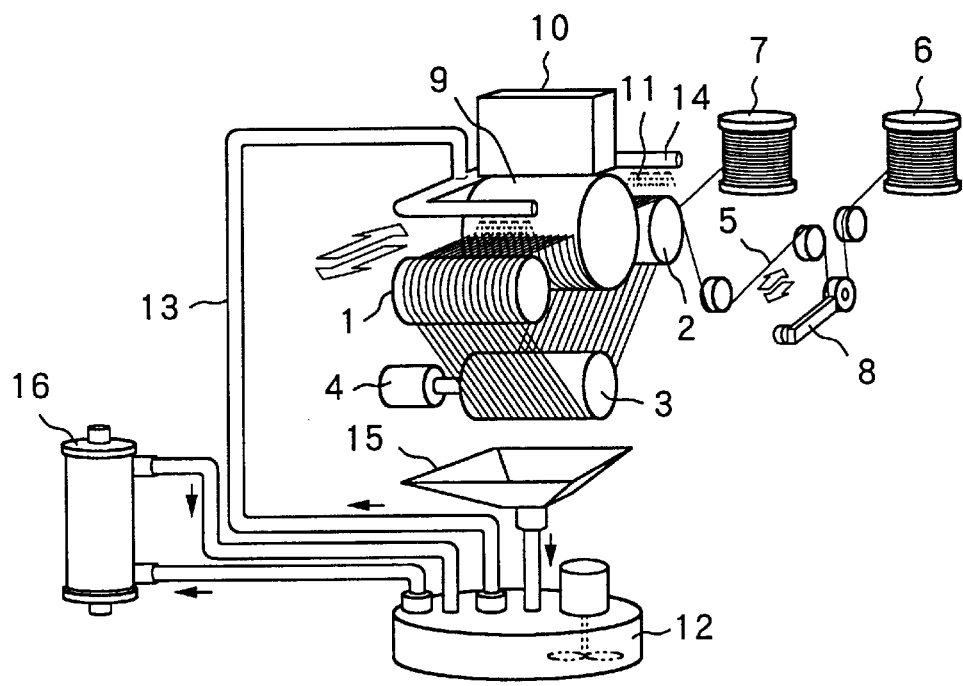
FIG. 1 is a schematic view illustrating a wire-sawing machine for slicing an ingot.
Figure 2:
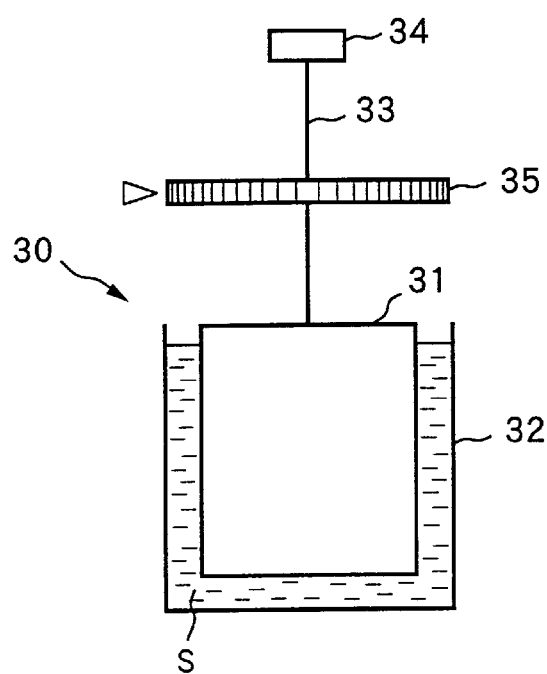
FIG. 2 is a sectional view for explanation of a axial cylinder type viscometer.

However, fluidization of slurry in a dynamic state during slicing is not made clear by a conventional slurry-evaluating test, and estimation using the measured viscosity, specific gravity and pH value is meaningless for actual slicing. For instance, when an ingot 9 is sliced by a wire 5 of 0.18 mm in diameter (as shown in FIG. 1), grooves of 0.24 mm width are formed in the ingot 9. Slurry 11 is fed to the wire 5 travelling through the grooves at a speed of 500 m/minute, and carried to deep parts of the grooves in accompaniment with the wire 5. Accounting for the fluidization of the slurry 11, viscosity of the slurry 11 is necessarily adjusted to a high level to assure adhesion of the slurry 11 to the high-speed travelling wire 5 without dropping. However, excessively high viscosity impedes supply and inflow of the slurry 11 into the narrow grooves. On the other hand, lower viscosity promotes smooth discharge of the slurry 11 from parts already sliced off. However, excessively low viscosity causes disintegration of grits from the slurry. Disintegrated grits causes sticking of cut-off wafers and plugging of slurry-supply pipings.

Due to fluidization of slurry during wire-saw slicing, viscosity of the slurry shall be determined to a proper value accounting a shear speed condition. A shear speed applied to the slurry is very high at a position where the wire 5 comes in contact with the ingot 9, while the shear speed is very low in a natural flowing state where gravity solely affects on the slurry.

Although various kinds of slurry are mostly the non-Newtonian type that viscosity varies in response to a shear speed, the viscosity has been measured so far by a axial cylinder type viscometer (Type-B viscometer) as aforementioned. A viscosity value measured by the axial cylinder type viscometer merely represents viscosity at a certain shear speed due to the structure of the axial cylinder type viscometer. In short, the non-Newtonian slurry can not be accurately evaluated by the axial cylinder type viscometer. In this regard, the inventors hit upon use of a cone and plate type viscometer (Type-E viscometer) for measuring viscosity at different rotor speeds, and research effects of slurry on slicing motion.

Figure 3:
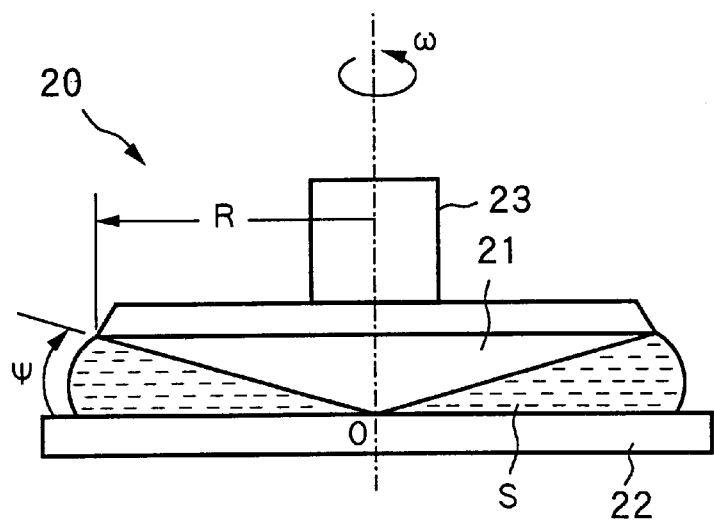
FIG. 3 is a sectional view for explanation of a cone and plate type viscometer.

The cone and plate type viscometer has structure illustrated in FIG. 3. In principal, an inner cylinder 31 of the axial cylinder type viscometer 30 is replaced by a cone 21. The cone 21 is of a conical shape with a cone angle $\phi$ at its lower side, and the cone angle $\phi$ is held within a small range of 20 minutes to 3 degrees. The cone 21 can be rotated along a direction (D by a rotary shaft 23. A disc 22 is concentrically located at a position in contact with a top of the cone 21. There is a narrow space between the cone 21 and the disc 22 due to the shape of the cone 21. The narrow space is filled with sample slurry S whose viscosity is to be measured. A small amount of the sample slurry S is enough to fill the narrow space.

When the cone 21 is rotated in the state that the narrow space is filled with the sample slurry S, a rotation force T (a torque) depending on the sample slurry S is applied to the disc 21. Since the rotation force T is proportional to viscosity of the sample slurry S, the viscosity is calculated from the rotation force T.

The cone and plate type viscometer has the feature that a shear speed D applied to the sample slurry S can be changed in proportion to a rotation speed N of the cone 21 driven by the rotary shaft 23. For instance, a cone and plate type viscometer used in our experiment had a cone 21 with a diameter of 10 mm and a cone angle $\phi$ of 1 degrees 43 minutes. In this case, a relationship of $D=3.8 \times N$ was established between a rotation speed N (r.p.m.) of the cone 21 and a shear speed D (/second) applied to the slurry sample S.

Slurry 11 is supplied to a wire 5 from a nozzle 14 (in FIG. 1). At this moment, the slurry moves as a natural flow due to gravity, so a shear speed applied to the slurry is tiny. Therefore, viscosity is measured at a low shear speed of 2/second or so, which is near a measurable lower limit of the cone and plate type viscometer 20.

On the other hand, the slurry 11, which is flowing into a space between a high-speed travelling wire 5 and an ingot 9, is affected by a high shear speed. In this regard, the slurry is testified to measure its viscosity at a high shear speed of 380/second or so, which is near a measurable upper limit of the cone and plate type viscometer.

The slurry exhibits the non-Newtonian property that its viscosity is higher in a stationary state but lower in a fluidizing state. The inventors has researched the relationship of the shear speed with the viscosity variable between the stationary and fluidized states, and found from a plenty of experiments that slurry suitable for wire-saw slicing is offered by adjusting its viscosity to approximately 400–700 mPa·second at a shear speed of approximately 2/second and to approximately 50–300 mPa·second at a shear speed of approximately 380/second.

Evaluation of the slurry is not limited to these two conditions, but viscosity of the slurry may be also measured at various shear speeds to more accurately forecast motion of the slurry during wire-saw slicing.

EXAMPLE

Four kinds of slurry A, B, X and Y were prepared to compositions shown in Table 1, included below and SiC grits were dispersed therein at a ratio of 50 wt. %.

Figure 4:
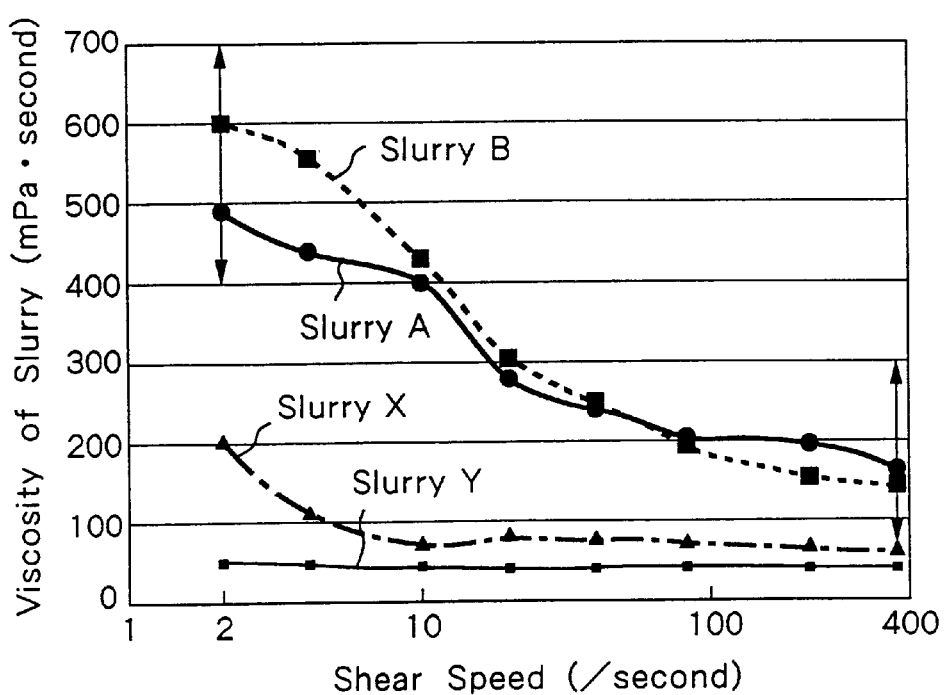
FIG. 4 is a graph illustrating a relationship between viscosity of slurry and a shear speed applied to the slurry.

Each slurry was evaluated according to the present invention. Each slurry A, B, X and Y was poured in a narrow space between a cone 21 and a disc 22 vessel of a cone and plate type viscometer 20 (Type-E viscometer), and its viscosity was measured at a shear speed of 2/second, 4/second, 10/second, 20/second, 40/second, 80/second, 200/second and 380/second, respectively. FIG. 4 shows measurement results in relationship with the shear speed. Viscosity of each slurry A and B was within a range of 400–700 mPa·second at a shear speed of 2/second and within a range of 50–300 mPa·second at a shear speed of 380/second. But, viscosity of each slurry X and Y did not fulfill these requisitions.

Each slurry A, B, X and Y was used for wire-saw slicing a silicon ingot 9 of 400 mm in diameter to wafers of 1.0 mm in average thickness. A steel wire of 0.18 mm in diameter was used as a wire 5. The ingot 9 was sliced by a bi-directional travelling method wherein the wire 5 traveled at a maximum speed of 750 m/second along one direction for 18 seconds and then reversally traveled along the opposite direction for 12 seconds.

TABLE 1

COMPOSITIONS OF SLURRY AND SLICING RESULTS

| NOTE | Kind of Slurry | Main Component | | Additives | | Results of slicing ingots | | |
|---|---|---|---|---|---|---|---|---|
| | | | | | | Dimensional Accuracy of Wafer (thickness variation) | Roughness of Wafer | Accumulation of Grits Between Wafers or In Wire-Sawing Machine During Slicing |
| Present Invention | A | Machine Oil | 97% | Inorganic Bentonite Surfactant | 1% 2% | 35 μm | 20 μm | no accumulation |
| | B | Glycol | 85% | Inorganic Bentonite Dispersing Agent | 0.5% 2% | 35 μm | 20 μm | no accumulation |
| Comparative Example | X | Glycol | 70% | Inorganic Bentonite | 0.5% | 40 μm | 25 μm | slight accumulation |
| | Y | Glycol | 70% | Dispersing Agent | 2% | 45 μm | 40 μm | heavy accumulation |

Properties of slurry useful for wire-saw slicing an silicon ingot is explained in the aforementioned Example. But, the explanation does not put any restrictions on the scope of the present invention, but the present invention is also applicable to slurry for wire-saw slicing a compound semiconductor block, a quartz block or the like in the same manner.

According to the present invention as aforementioned, viscosity of slurry is adjusted to a specified relationship with a shear speed. Such slurry is efficiently fed even to deep parts of grooves formed in an ingot or the like and consumed for wire-saw slicing thereof, since it fulfils requisitions necessary for smooth fluidization in the grooves. Consequently, the ingot can be sliced to wafers or discs good of dimensional accuracy with high performance. Since properties of the slurry suitable for smooth fluidization are previously proven without necessity of an ingot-slicing test, cost and time spent for examination of new slurry are remarkably reduced.

What is claimed is:

1. A method of evaluating slurry useful for wire-saw slicing comprising the steps of:

providing a viscometer which has a cone held in contact with a disk at the lower end of said cone to form a narrow gap for pouring said slurry therein, measuring viscosity of said slurry under conditions different in a shear speed by changing a rotation speed of said cone, to forecast dynamic motion of said slurry during wire-saw slicing, and evaluating said slurry, wherein said slurry exhibits viscosity of 400–700 mPa·second at a shear speed of 2/second and of 50–300 mPa·second at a shear speed of 380/second.

* * * * *